United States Patent [19]

MacLauchlan et al.

[11] Patent Number: 5,511,424
[45] Date of Patent: Apr. 30, 1996

[54] REMOTE PREAMPLIFIER AND IMPEDANCE MATCHING CIRCUIT FOR ELECTROMAGNETIC ACOUSTIC TRANSDUCER

[75] Inventors: Daniel T. MacLauchlan; Karl C. Henderson; John H. Flora, all of Lynchburg, Va.

[73] Assignee: The Babcock & Wilcox Company, New Orleans, La.

[21] Appl. No.: 196,661

[22] Filed: Feb. 15, 1994

[51] Int. Cl.[6] .................................................. G01N 29/04
[52] U.S. Cl. ............................................ 73/609; 73/610
[58] Field of Search ............................ 73/609, 610, 620, 73/643, 658, 661, 629, 633

[56] References Cited

U.S. PATENT DOCUMENTS

| | | | |
|---|---|---|---|
| 3,982,425 | 9/1976 | McLain | 73/635 |
| 4,202,210 | 5/1980 | Multon et al. | 73/194 |
| 4,229,666 | 10/1980 | Milburn, Jr. | 307/290 |
| 5,303,591 | 4/1994 | Dykes et al. | 73/620 |
| 5,309,765 | 5/1994 | Horigome et al. | 73/620 |

OTHER PUBLICATIONS

U.S. Pat. Application Ser. No. 08/196,662, Our Case 5432 filed Feb. 15, 1994.

*Primary Examiner*—Richard Chilcot
*Assistant Examiner*—Max Noori
*Attorney, Agent, or Firm*—Daniel S. Kalka; Robert J. Edwards

[57] ABSTRACT

A preamplification and impedance matching circuit for an electromagnetic acoustic transducer includes an impedance matching section of the circuit having input terminals for receiving radio frequency power from a radio frequency power source. A matching transformer, which is a step-down transformer, is operatively connected to the input terminals. Diode networks are operatively connected to the matching transformer and output terminals which lead to the coil of the transducer. Signal responses emitted by the transducer coil are transmitted to a preamplifier section of the circuit. Choke coils or resistors are used to limit radio frequency power entry into the preamplifier section of the circuit. The preamplifier section has a preamplifier which is operatively connected to a first transformer and a second transformer such that the transformer are located on opposite sides of the preamplifier for increasing the amplitude of the coil signal response prior to transmission to detectors located in the instrumentation of the transducer.

12 Claims, 4 Drawing Sheets

REMOTE PREAMPLIFIER AND IMPEDANCE MATCHING CIRCUIT FOR ELECTROMAGNETIC ACOUSTIC TRANSDUCER

BACKGROUND OF THE INVENTION

1. Field of the Invention

The present invention relates, in general, to electromagnetic acoustic transducers and, in particular, to a new and useful preamplifier and impedance matching circuit for electromagnetic acoustic transducers.

2. Description of the Related Art

Electromagnetic acoustic transducer (EMAT) systems have been developed and are used in an increasing number of applications, such as nondestructive examinations through many industries. EMATs perform ultrasonic inspections without the use of a fluid couplant which is required with conventional piezoelectric ultrasonic transducers. Inspection with EMATs is faster and more reliable than conventional transducers; and EMAT inspection is easy to automate.

A majority of EMAT applications use meanderline coils to generate acoustic waves directly in the metal components being inspected. Optimum response from EMATs which use these coils requires the generation of a burst of radio frequency (RF) alternating current to induce the ultrasonic waves at the coil. Peak currents of 100 to 200 amperes are required for the most effective use of the meanderline EMAT coils. The RF tone burst is presently provided by a commercially available RF power amplifier. Since these amplifiers have an output impedance of 50 ohms, an impedance matching circuit is required to generate the highest levels of excitation current. The EMAT instrumentation also performs the function of amplifying, filtering and detecting the response signals which occur when ultrasonic waves are reflected back to the EMAT coil due to defects.

If an application requires that the EMAT has to be used at distances of more than a few feet from the EMAT instrumentation, the sensitivity of the system can be decreased substantially. This decrease in sensitivity can be attributed to several factors including cable losses, less than optimum impedance matching and electromagnetic interference from external sources.

Presently, there is no known device which eliminates these above-listed deficiencies.

SUMMARY OF THE INVENTION

The present invention pertains to electromagnetic acoustic transducers (EMATs). The present invention provides a remote preamplifier and impedance matching circuit for an EMAT which is attached and connected to the instrumentation of the EMAT.

It is an object of the present invention to provide a remote preamplifier and impedance matching circuit for an EMAT which decreases radio frequency (RF) power losses in the cables used in the EMAT instrumentation.

It is another object of the present invention to provide a circuit which minimizes impedance mismatching between an RF power amplifier and the coil of an EMAT for a wide range of cable lengths in order to maximize the excitation power transmitted to the EMAT coil.

It is another object of the present invention to provide remote operation of the EMAT from the primary instrumentation of the EMAT at distances greater than 50 feet without experiencing a significant loss in sensitivity.

It is another object of the present invention to provide a circuit for an EMAT which substantially reduces electromagnetic interference in the EMAT signal response due to external sources.

It is another object of the present invention to provide a circuit for an EMAT which is compact and light-weight, and which is an integral part of the EMAT while providing little increase in the total size and weight of the EMAT.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

The present invention is a remote preamplifier and impedance matching circuit for use with EMATs which is a compact, light-weight circuit which contains relatively few components.

Figure 1:
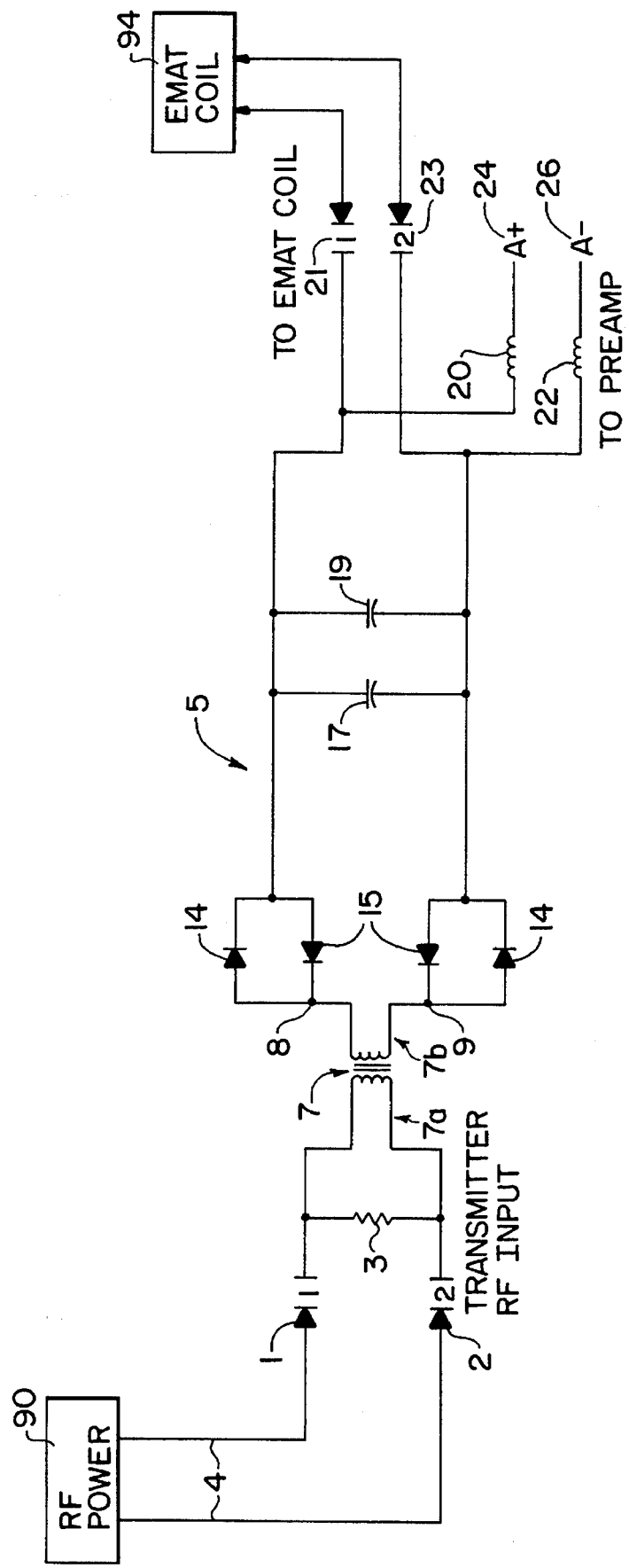
FIG. 1 is a schematic diagram illustrating an impedance matching network section of a circuit according to the present invention.

FIG. 1 illustrates an impedance matching network section, generally designated 5, of the circuit according to the present invention. The matching network section 5 is used in conjunction with a radio frequency (RF) power source 90, such as an RF power amplifier, and a cable 4 of the power source 90. Cable 4 normally has a 50 ohm impedance.

The matching network circuit 5 has terminals 1 and 2 operatively connected to the cable 4 of the RF power source 90 for receiving RF power from the RF power source 90. During a typical operation of an EMAT, a burst of RF power from source 90 is applied through cable 4 through terminals 1 and 2. A resistor 3 is operatively connected between terminals 1 and 2, and the RF power is provided to a matching transformer 7 having a primary side 7a and a secondary side 7b. The primary side 7a of transformer 7 is operatively connected to terminals 1 and 2 for receiving the RF power.

Matching transformer 7 is a step-down transformer with a turns ratio typically ranging from 2 to 5. The matching transformer 7 matches the 50 ohm impedance of cable 4 to the impedance of the parallel combination of tuning capacitors 17 and 19 and an EMAT coil 94.

Diode networks 14 and 15 are operatively connected to leads 8 of the secondary side 7b of matching transformer 7.

Figure 3:
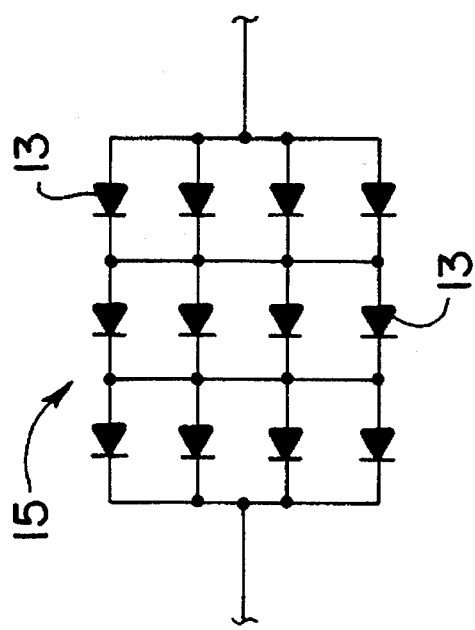
FIG. 3 is a schematic view of a second diode network of FIG. 1.
Figure 2:
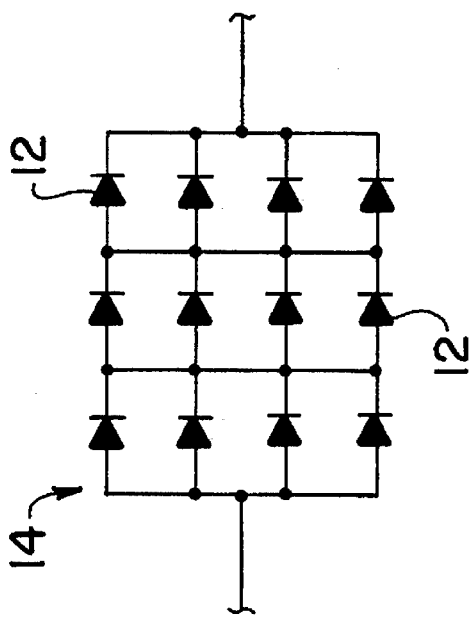
FIG. 2 is a schematic view of a diode network of FIG. 1.

As shown in FIG. 2, diode network 14 comprises a plurality of diodes 12, oriented in the same direction, i.e. anode to cathode, and aligned in series and parallel. FIG. 3 illustrates diode network 15 comprising a plurality of diodes 13, oriented in the same direction, but in an opposite direction of diodes 12 (FIG. 2), and aligned in series and parallel.

Diodes 12 (FIG. 2) and 13 (FIG. 3) provide for isolation of the EMAT coil 94 (FIG. 1) and a preamplifier circuit 10 (FIG. 4) from the power amplifier 90 after the burst of RF excitation has been applied by power amplifier 90. Diodes 12 and 13 only pass current which have driving voltages in excess of approximately 4 volts and limit currents with driving voltages which are less than this value. Noise from input cable 4 and amplifier 90 are decreased by several orders of magnitude. Also, the relatively small signal response from the EMAT coil 94, which is typically a few microvolts, is not decreased by the loading of input cable 4 and RF amplifier 90 since the diodes 12 and 13 will have a high impedance when the voltage across their terminals are small.

As shown in FIG. 1, RF power is provided through diode networks 14 and through tuning capacitors 17 and 19 which are aligned in parallel, and in turn provided to outputs 21 and 23 which are operatively connected to an EMAT coil 94.

Outputs 24 and 26 are also operatively connected to choke coils 20 and 22 which block or limit RF power transmitted by diode networks 14. Output terminals 24 and 26 receive coil signals emitted by the EMAT coil 94 and provide the signals to the preamplifier section 10 of the circuit, as shown in FIG. 4, at terminals 24a and 26a, respectively.

Figure 5:
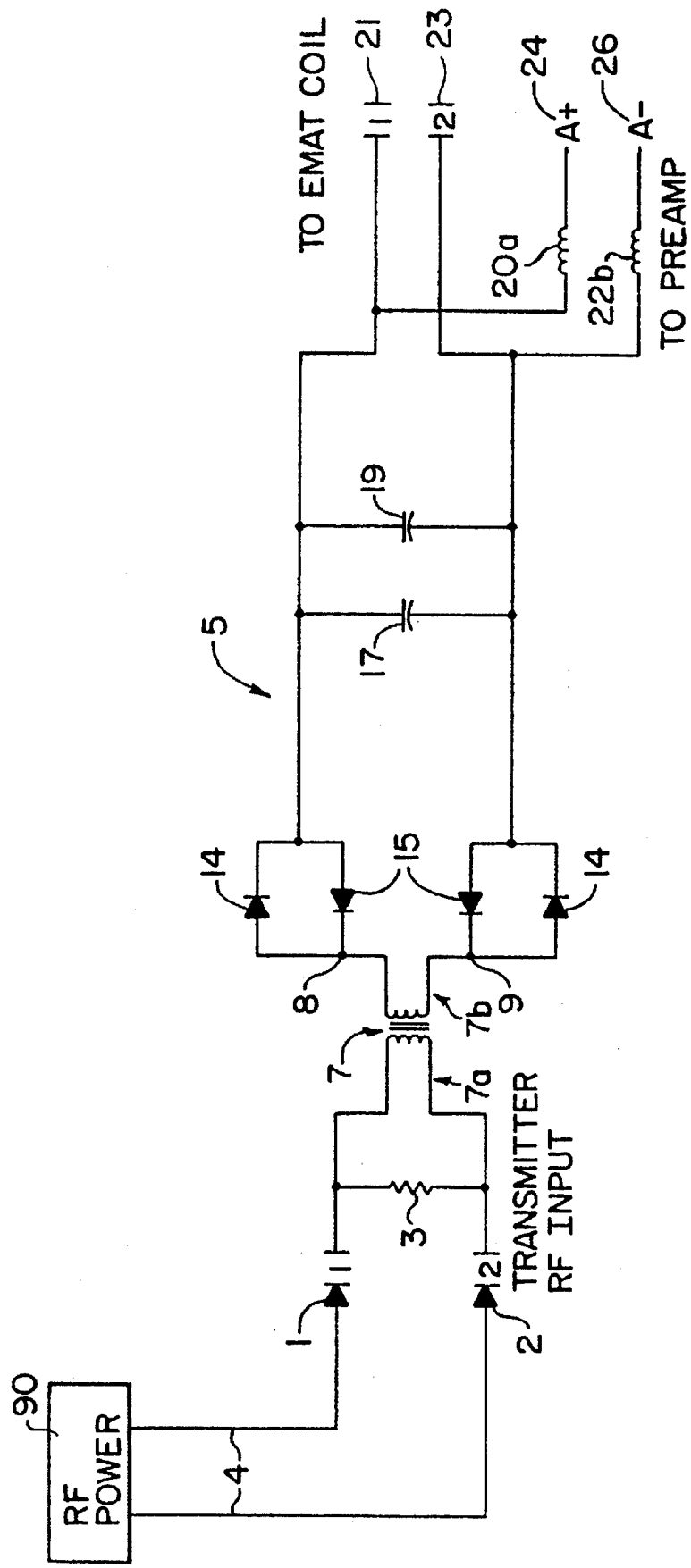
FIG. 5 is a second embodiment of the section of FIG. 1.

Chokes 20 and 22 (FIG. 1) are coils, which protect the receiver amplifier 10 during the RF excitation and provide for minimum thermal noise due to their low resistance. Inductors 20 and 22 can be replaced with resistors 20a and 22a, as shown in FIG. 5, in cases where the signal response from the EMAT coil is much greater than the thermal noise.

Figure 4:
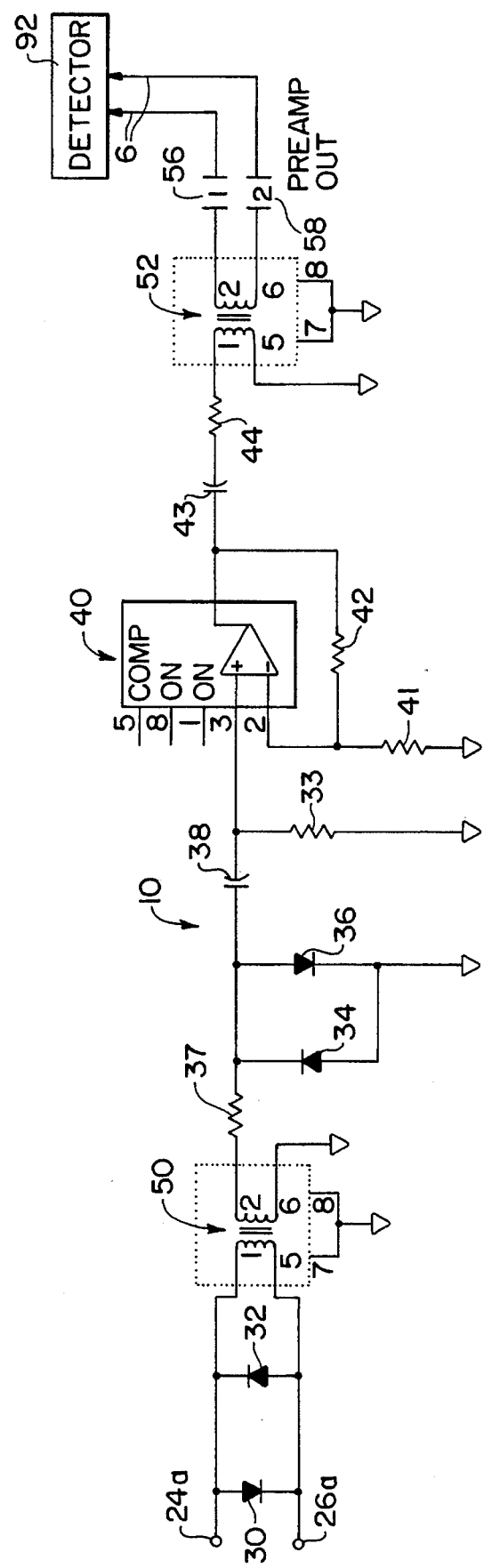
FIG. 4 is a schematic diagram of a preamplification section of the circuit according to the present invention.

As shown in FIG. 4, terminals 24a and 26a of the preamplifier circuit 10 receive the EMAT coil signals which are in turn provided to input diodes 30 and 32 which are arranged in parallel and operatively connected between terminals 24a and 26a and a transformer 50. Input diodes 30 and 32 also work to limit the RF power applied to the preamplifier circuit 10 during RF excitation.

The EMAT coil signal response is transmitted through transformer 50 through resistor 37 and through a second pair of diodes 36 and 34 which are also arranged in parallel and oriented in opposite directions.

A preamplifier 40 is operatively connected to transformer 50 in the preamplifier circuit 10. A second pair of diodes 34 and 36 are operatively connected between transformer 50 and preamplifier 40 and arranged in parallel and oriented in opposite directions. Diodes 34 and 36 are used in conjunction with resistor 37 for providing additional protection of preamplifier 40 from RF excitation. Also, a capacitor 38 and resistor 33 are operatively connected between transformer 50 and preamplifier 40.

A second transformer 52 is operatively connected to preamplifier 40 at a side opposite transformer 50 of the circuit 10. Transformer 52 is operatively connected to output terminals 56 and 58 which are in turn operatively connected to cable 6 which leads to detector 92 for detecting the EMAT coil signals.

Resistors 41, 42 and 44 are used in conjunction with capacitor 43 at preamplifier 40 and transformer 52 of the circuit 10.

The preamplifier section 10 of the circuit according to the present invention, as shown in FIG. 4, increases the amplitude of the EMAT coil signal response by approximately a factor of 100, i.e., 100×, and provides sufficient power to transmit the coil signal to detector 92 which is located in the EMAT instrumentation. This amplification increases most signal responses to levels which are much greater than the electromagnetic interference (EMI) signals which might enter instrumentation through the shielding on the receiver cables 6. Amplification of the EMAT signal response prior to transmission on cables 6 improves the signal-to-EMI noise ratio and thereby reduces the number of false indications experienced by the EMAT instrumentation.

Transformers 50 and 52 of circuit section 10 provide voltage amplification, common mode rejection and isolation from inherent ground loops. As with known signal amplifiers, preamplifier 40 requires +/– 5 volt, DC power.

While specific embodiments of the invention have been shown and described in detail to illustrate the application of the principles of the invention, it will be understood that the invention may be embodied otherwise without departing from such principles.

What is claimed is:

1. A circuit for an electromagnetic acoustic transducer having a coil, a radio frequency power source and detection means for detecting signals transmitted by the coil, the circuit comprising:

input means operatively connected to the radio frequency power source for receiving the radio frequency power;

a matching transformer having a primary side and a secondary side, the primary side of the matching transformer being operatively connected to the input means;

diode means operatively connected to the secondary side of the matching transformer;

connection means operatively connected with the diode means and the coil of the electromagnetic acoustic transducer for providing the radio frequency power to the coil and for receiving a signal transmitted by the coil;

preamplifier input means operatively connected to the connection means for receiving the signals transmitted by the coil;

blocking means operatively connected between the preamplifier input means and the connection means for blocking the radio frequency power;

a first transformer operatively connected to the preamplifier input means;

a first pair of diodes operatively connected in parallel between the preamplifier input means and the first transformer, one diode being in a direction opposite to the other diode;

a preamplifier operatively connected to the first transformer;

a second transformer operatively connected to the preamplifier; and output means operatively connected to the second transformer and the detection means for outputting the signal transmitted by the coil to the detection means.

2. The circuit according to claim 1, wherein the diode means comprises a plurality of networks, each network having a plurality of diodes.

3. The circuit according to claim 2, wherein the two pairs of networks are operatively connected to the secondary side of the matching transformer.

4. The circuit according to claim 3, wherein each pair of networks has one network having all of the diodes in a first direction and another network having all of the diodes in a second direction opposite the first direction.

5. The circuit according to claim 1, wherein the connection means includes a pair of tuning capacitors in parallel.

6. The circuit according to claim 1, wherein the blocking means comprises a plurality of choke coils.

7. The circuit according to claim 1, wherein the blocking means comprises a plurality of resistors.

8. The circuit according to claim 1, including a resistor operatively connected between the first transformer and the preamplifier.

9. The circuit according to claim 8, including a second pair of diodes operatively connected in parallel between the resistor and the preamplifier.

10. The circuit according to claim 4, wherein the diodes pass current which is greater than 4 volts.

11. The circuit according to claim 1, wherein the amplitude of the coil signal outputted by the output means is 100× greater than the amplitude of the coil signal provided to the preamplifier input means.

12. The circuit according to claim 1, wherein the matching transformer is a step-down transformer.

* * * * *